US005546938A

United States Patent [19]
McKenzie

[11] Patent Number: 5,546,938
[45] Date of Patent: Aug. 20, 1996

[54] ICU PATIENTS VENTILATOR TUBE HOLDING DEVICE

[76] Inventor: Shirley T. McKenzie, 1159 Olive Lake Dr., St. Louis, Mo. 63132

[21] Appl. No.: 518,821

[22] Filed: Aug. 24, 1995

[51] Int. Cl.⁶ .................................................. A61M 16/00
[52] U.S. Cl. ............................ 128/207.17; 128/DIG. 26; 604/180
[58] Field of Search ................... 128/207.14, 207.17, 128/207.18, DIG. 26; 604/174, 180, 263; 428/40, 41, 42, 43, 343; 156/510; 24/DIG. 11

[56] References Cited

U.S. PATENT DOCUMENTS

| | | | |
|---|---|---|---|
| 3,927,676 | 12/1975 | Schultz | 128/DIG. 26 X |
| 4,447,482 | 5/1984 | Heinzelman et al. | 428/42 |
| 5,221,265 | 7/1993 | List | 604/180 |
| 5,306,233 | 4/1994 | Glover | 602/41 |

*Primary Examiner*—Stephen Funk
*Assistant Examiner*—Eric P. Raciti
*Attorney, Agent, or Firm*—Polster, Lieder, Woodruff & Lucchesi, L.C.

[57] ABSTRACT

A device (10) for attaching and tube (V). The tube inserted in a person's mouth or nose to provide a ventilation and suction passage for the person. One end of the tube is inserted in the person's mouth or the end of a nasal passage and the other end of the tube protrudes out of the mouth or nasal passage. An elongate piece (12) of material has a length sufficient for the device to fit behind the person's head with the ends of the piece reaching across a portion of their face for use in securing the tube in place. Respective ends (14, 16) of the material are perforated so each end can be separated into at least two parallel strips (14a, 14b, 16a, 16b). The separable portions of the ends forming the respective strips extend longitudinally of the piece of material. The respective outer ends of the strips are spatially separable from each other so each strip can be separately used to either wrap about the ventilator tube or the person's face to position and hold the tube in place and prevent the ventilator tube from being intentionally or inadvertently dislodged. A removable cover (32) covers the strips prior to their being positioned on the person's face or the tube. The strips are of an adhesive material, and the cover covers the adhesive material until removed by a user prior to use of the device. This makes the device easy to fit about a person's head, the cover being left in place when the device is so fitted. The cover on each strip is removed for the strips to be used in fitting the ventilator tube in place.

7 Claims, 2 Drawing Sheets

ICU PATIENTS VENTILATOR TUBE HOLDING DEVICE

BACKGROUND OF THE INVENTION

This invention relates to ventilator or breathing tubes used with medical patient's, especially persons brought into emergency rooms or patient's in intensive care units, and more particularly, to a ready to use, disposable, device for securing the tube in a patient's mouth or nostril to maintain the tube in place and prevent its dislodgment.

Oral and nasal endotracheal tubes are used, particularly in intensive care and emergency room situations to insure a patient's airways are clear for proper breathing and ventilation. In many instances, endotracheal or ET tubes are used in conjunction with ventilators, suction devices, etc. to provide vital treatment for a patient. Tube intubation usually requires use of some type of securement to prevent the tube from being dislodged or extubated. Unplanned extubations can be extremely harmful to the patient, and can occur as a result of the patient's movements such as when the patient pulls out the tube became of the discomfort it is causing him or her. Or, the tube may be inadvertently dislodged by the medical staff treating during patient treatment. See, for example, Techniques for preventing and managing unplanned extubations, The Journal of Critical Illness, Vol.9. No. 6, June, 1994, pages 609–619. As pointed out therein, estimates are that 15 million intubations are performed annually. Of these, unplanned extubations account for a significant number of extubations in critically ill patients (ibid. at p. 610).

The problem of adequately securing an endotracheal tube has been recognized in the art. See, for example, U.S. Pat Nos. 5,237,988, 5,038,778, 4,906,234, 4,844,061, 4,326, 515, 4,313,437, and 3,927,676. In each instance. the particular device employed is intended to maintain a tube in place. However, while these devices may accomplish their purpose, they do not necessarily do so in the most expeditious, easy to use manner that allows emergency room or intensive care personnel to intubate a patient when the need arises. The present invention provides a simple, low cost, easy-to-use device for attaching, holding, and maintaining an endotracheal tube in place.

SUMMARY OF THE INVENTION

Among the several objects of the present invention may be noted the provision of a device for attaching and holding a ventilator tube such as an endotracheal tube in a patient's mouth or the end of a nasal passage;

the provision of such a device for use in intensive care units and hospital emergency rooms by medical personnel to provide an air passage for breathing and a suction port for removing foreign matter and other diseased or unwanted matter from the patient's body;

the provision of such a device which is available in a sterilized, prepackaged form for ready availability and use by medical personnel;

the provision of such a device which is foraged of a strip of material such as a cloth material with the respective ends of the device being separable into strips for the strips to be used in securing a ventilator tube in place in a patient's mouth or nose;

the provision of such a device in which the material is made of, or is coated with, an adhesive material thereby to facilitate attachment of portions of the strips to a ventilator tube and/or to the side of the patient's face to secure the tube in place;

the provision of such a device in which the center portion of the material is covered with a non-adhesive backing material for the center portion of the device to fit behind the patient's head when the device is being applied and not irritate the back of the person's head, or stick to their hair, the adhesive strips being covered with a peel off cover which is not removed until the ventilator tube is to be fitted in place;

the provision of such a device in which the material is an elasticized or stretch material having sufficient play so medical personnel can easily manipulate the strips when fixing a ventilator tube in place;

the provision of such a device to be available in a variety of sizes so the device can be readily used with children as well as adults whose head size varies considerably;

the provision of such a device which makes it difficult for a patient to remove the device, so a ventilator tube will remain in place once inserted, but which is readily movable by medical personnel when desirable;

the provision of such a device which is portable so a nurse, nurse's aide, or doctor can easily carry the device in a pocket of their garments; and, the provision of such a simple, low cost, device which is readily applied and easier to use than prior appliances of a similar type and which allows medical personnel to easily attach, hold, and maintain a ventilator or an endotracheal tube in place.

In accordance with the invention, generally stated, a device is provided for attaching and holding a ventilator tube. The tube is inserted in a person's mouth or nose to provide a ventilation and suction passage for the person. One end of the tube is inserted in the person's mouth or the end of a nasal passage and the other end of the tube protrudes out of the mouth or passage. An elongate piece of material has a length sufficient for the device to fit behind the person's head with the ends of the piece reaching across a portion of their face for use in securing the tube in place in the mouth or nose. Respective ends of the material are perforated so each end can be separated into at least two parallel strips. The separable portions of the ends forming the respective strips extend longitudinally of the piece of material. The respective outer ends of the strip are spatially separable from each other so each strip can be separately used to either wrap about the ventilator tube or the person's face to position and hold the tube in place and prevent the ventilator tube from being intentionally or inadvertently dislodged. A removable cover covers the strips prior to their being separated. The strips are of an adhesive material, and the cover covers the adhesive material until removed by a user prior to use of the device. This makes the device easy to fit about a person's head, the cover being left in place when the device is so fitted. The cover on each strip is then removed for the strips to be used in fitting the ventilator tube in place. Other objects and features will be in part apparent and in part pointed out hereinafter.

BRIEF DESCRIPTION OF THE DRAWINGS

Corresponding reference characters indicate corresponding parts throughout the drawings.

DESCRIPTION OF A PREFERRED EMBODIMENT

Figure 1:
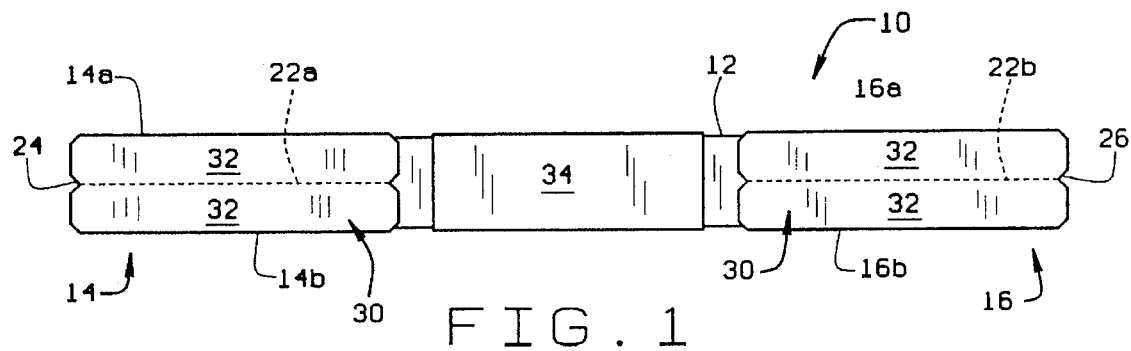
FIG. 1 is a plan view of a device of the present invention for securing a ventilator tube in place.
Figure 2:
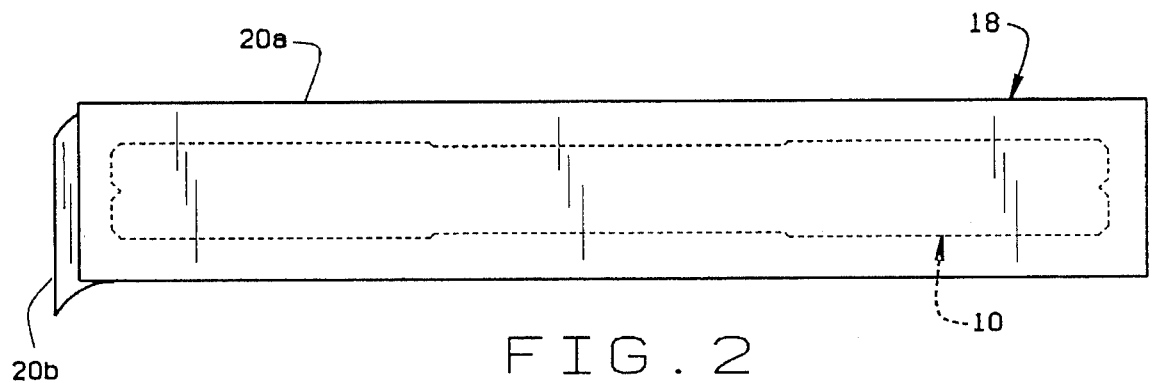
FIG. 2 is a plan view of the device as packaged.
Figure 6:
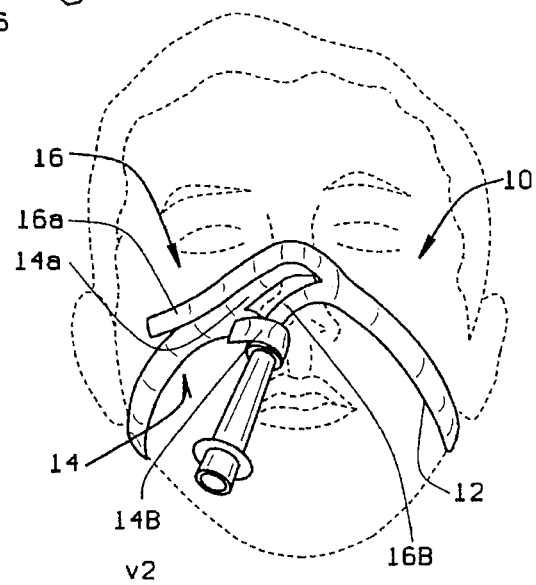
Figure 5:
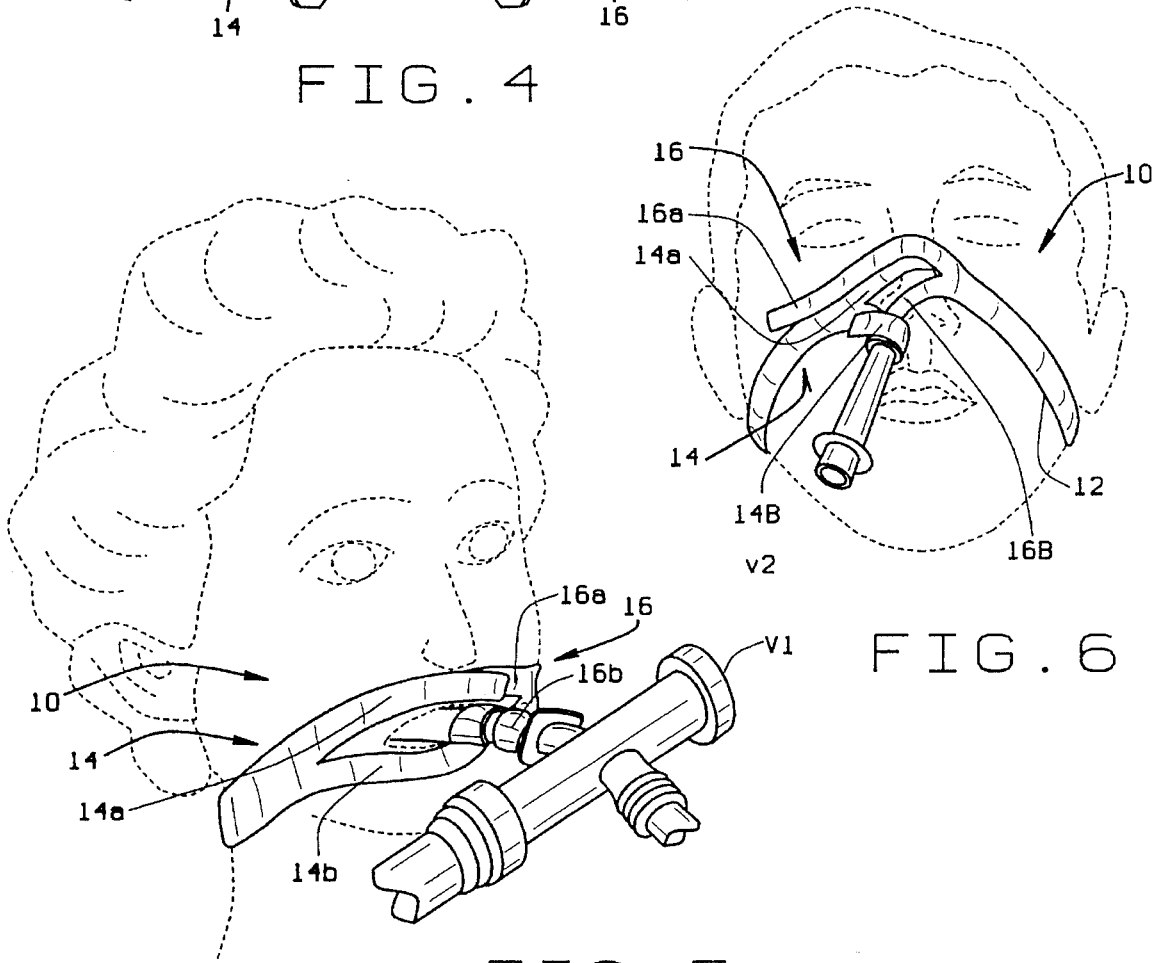
FIG. 5 is representation of the device securing a ventilator tube in a person's mouth; and, FIG. 6 is a similar representation to FIG. 5 for securing the tube in a person's nose.

Referring to the drawings, a device of the present invention is indicated generally 10 in FIG. 1. Device 10 is used for attaching and holding a ventilator tube V which is inserted in the mouth or nose of a person. Referring to FIG. 5, one type of ventilator tube V1 is shown inserted in a person's mouth and held in place using device 10. In FIG. 6, a second type ventilator tube V2 is shown inserted in a nostril so to be positioned in a nasal passage. Again, the ventilator tube is held in place using the device. The use of ventilator tubes or endotracheal (ET) tubes commonly occurs in hospital emergency rooms or intensive care units. Tubes are put in place to provide a ventilation and suction passage for the person. Ventilator tubes V1 or V2 typically include an elongate hollow cylinder forming an air or fluid passage. In addition, some of the tubes (for example, tube V1 in FIG. 5) have an intersecting passage which connects to an air hose, fluid drainage tube, etc. Regardless, one end of the ventilation tube is inserted in the person's mouth or nostril. The other end of the tube protrudes out of the mouth or nasal passage once the tube is in place. As noted in the aforementioned article, dislodgment of the tube, whether intentionally by a patient, or inadvertently by the patient or medical personnel, can have bad consequences. Device 10 is intended to so secure the ventilator tube in place that dislodgment cannot occur.

As shown in FIG. 1, device 10 includes an elongate piece 12 of material which is preferably a cloth material that is a stretchable or elasticized piece of material. The device is also either formed of an adhesive material, or it is coated with an adhesive. The length of the piece of material is sufficient for device 10 to be fined behind a person's head with the ends 14, 16 of the piece reaching across at least a portion of the person's mouth or nose for use in securing a ventilator tube in place in the mouth or nose. This is as shown in FIGS. 5 and 6. It will appreciated that device 10 may be made in a variety of different sizes so as to be usable with children as well as adults. Also, device 10 is prepackaged in a sterile package 18 and the device is in a sterilized condition when packaged. The package is, for example, a peel apart package comprised of opposed strips 20a, 20b sealed together, but readily separable by peeling one of the strips away from the other. Package 18 can conveniently be carded in a pocket (not shown) of a garment (also not shown) so medical personnel working in emergency rooms and intensive care units can carry a supply of the devices with them, if desired. Or, the packages can be conveniently stored.

Figure 3:
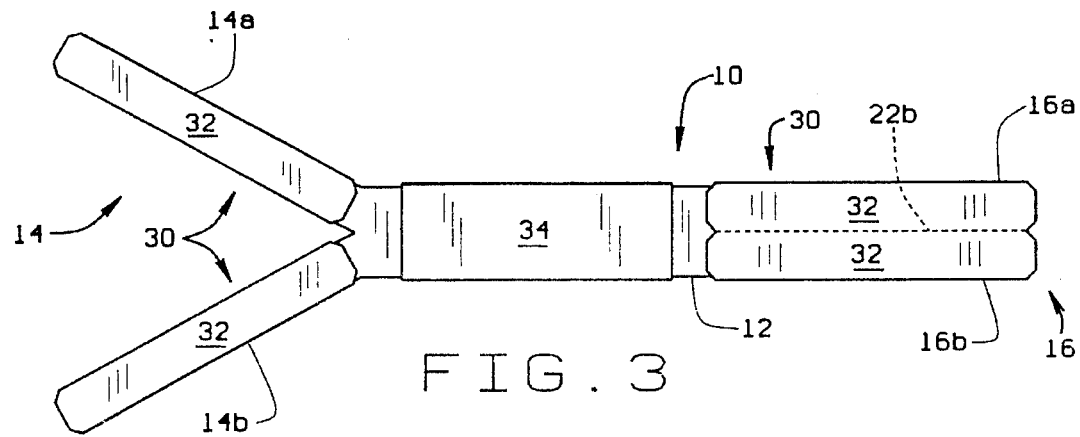
FIG. 3 is a plan view of the device with strips on one end of the device separated for use in securing a ventilator tube in place
Figure 4:
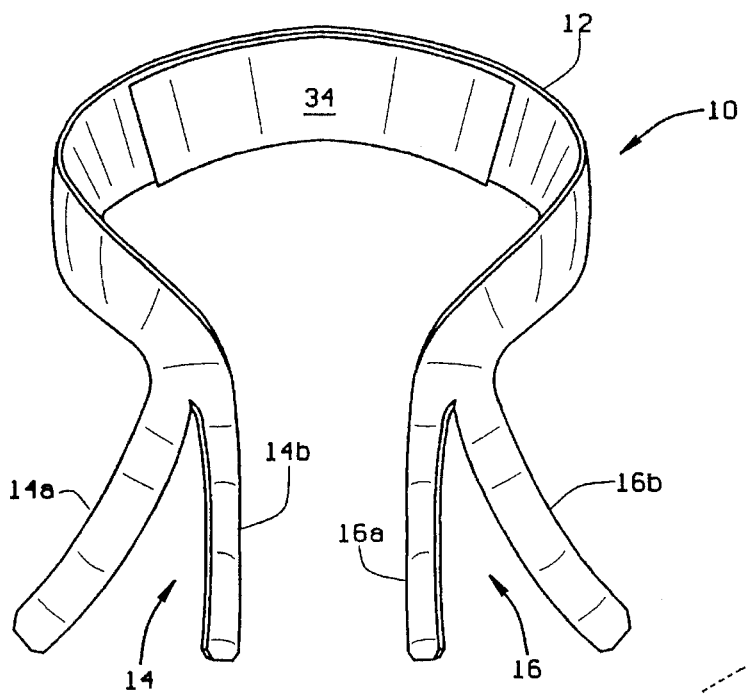
FIG. 4 is a perspective view of the device when prepared for use.

Device 10 includes perforation means 22a, 22b which allows respective ends 14, 16 of the material to be separated into at least two parallel strips, 14a, 14b, and 16a, 16b respectively. The perforation means may comprise a spaced series of perforations extending inwardly from the respective ends of the material toward the middle portion of the material. Preferably, the perforations are formed along the longitudinal centerline of the piece of material so the resulting width of each of the strips is the same. Or, instead of perforations, the perforation means may comprise an inwardly extending portion of material whose thickness is significantly less that of the rest of the material. This would create respective lines of weakness in the material which would readily tear when a pulling pressure is applied to respective ends of the strips. It will be noted that the respective corners of the strip are chamfered, and respective notches 24, 26 are formed in the ends of the piece of material at the location of the perforations or lines of weakness. The notches make it easier for one using the device to grasp the outer end of adjacent strips and separate them by pulling on the ends of the strips in opposite directions. As shown in FIGS. 3 and 4, the respective outer ends of the strip are spatially separable from each other. This permits each strip to be separably usable to wrap about a protruding portion of a ventilator tube V1 or V2, or about the person's face, to position and hold the ventilator tube in place and make it difficult for the ventilator tube to be intentionally or inadvertently dislodged.

As noted, the material of which device 10 is formed is either adhesive or has an adhesive backing. A cover means 30 includes a peel-away strip 32 of a plastic, non-adhesive material which is shaped to fit over each of the respective strips. In addition, the cover means includes a non-elastic pad 34 which fits over the center portion of the strip 12 of material. Pad 34 allows the device to be comfortably fitted behind a person's head without sticking to their skin or pulling their hair. Pad 34 is a permanent pad, while the strips 32 are removable once the device is in place.

Referring to FIGS. 4–6, the application of device 10 first involves its removal from package 18. Next, the strip of material is fitted behind the person's head with pad 34 being centered. As noted, the pad prevents the device from sticking to the person's skin or hair. When the ends of the device are positioned generally as shown in FIG. 4, the respective strips 14a, 14b, 16a, and 16b, are separated from each other and the covers 32 peeled off the strips to expose their adhesive surface. Typically, two opposed strips are wrapped about the ventilator tube, and the other two opposed strips are drawn across the person's face from opposite directions. In FIGS. 5 and 6, opposed strips 14a, 16a are pulled across the person's face, from opposite sides of the face. Opposed strips 14b, 16b are wrapped about the ventilator tube. The result is that the tube is securely positioned in the person's mouth or nose by the one pair of strips, with the other pair of strips, which are attached to his or her face, prevent the tube from being pulled out of place. When the ventilator tube is to be removed, the strips holding the tube are pulled away, as are the strips covering the face. Or, the strips can be cut with a scissors to free the tube for removal.

What has been described is a device for attaching and holding a ventilator tube such as an endotracheal or ET tube in a patient's mouth or nasal passage. The device can be used anywhere, but is especially useful in hospital emergency rooms and intensive care units. The device is used to hold a ventilator tube in place so to provide an air passage for a patient's breathing and also as suction port for removing unwanted material from the patient's body. The device is available in a sterilized packages and in different sizes for easy use with both children and adults. As packaged, the device can be carried in a nurse's or doctor's garment for ready availability. The device comprises a continuous strip of an adhesive material with the respective ends of the piece being covered with a peel off cover to facilitate placement of the device about a person's head. The center portion of the device is permanently covered with a non-adhesive material. The ends of the material are readily separarable into strips and the strips are used to secure a ventilator tube in place in a patient's mouth or nose. By being non-adhesive, the middle portion of the device will not stick to or irritate the back of the patient's head. The material may also be an elasticized or stretch material having sufficient play so medical personnel can easily manipulate the strips when fixing a ventilator tube in place. Use of the device makes it difficult for a patient to remove a ventilator tube, so the tube will stay in unless removed by medical personnel. The device is simple, low cost, and easy-to-use so a nurse or doctor can readily attach and hold a ventilator or endotracheal tube in place.

In view of the foregoing, it will be seen that the several objects of the invention are achieved and other advantageous results are obtained.

As various changes could be made in the above constructions without departing from the scope of the invention, it is intended that all matter contained in the above description or shown in the accompanying drawings shall be interpreted as illustrative and not in a limiting sense.

Having thus described the invention, what is claimed and desired to be secured by Letters Patent is:

1. A device for attaching and holding a ventilator tube inserted in the mouth or nose of a person in place to provide a ventilation and suction passage for the person, the ventilator tube including an elongate hollow cylinder one end of which is inserted in the person's mouth or the end of a nasal passage and the other end of which protrudes out of the mouth or nasal passage once the tube is in place, comprising:

an elongate piece of material the length of which is sufficient for the device to be fitted behind the person's head with the ends of the piece reaching across at least a portion of the person's mouth or nose for use in securing a ventilator tube in place in the mouth or nose;

perforation means allowing the respective ends of the material to be separated into at least two parallel strips, the separation between the strips extending along the longitudinal centerline of the piece of material with the separable portions of the ends of the piece forming the respective strips extending longitudinally of the piece of material with notches being formed in the respective ends of the piece of material at a junction between the respective strips for separating the strips by grasping the respective ends of adjacent strips and pulling them in opposite directions, the respective outer ends of the strip being spatially separable from each other for each strip to be separably usable to wrap about a protruding portion of the ventilator tube or about the person's face to position and hold the ventilator tube in place and make it difficult for the ventilator tube to be intentionally or inadvertently dislodged; and, removable cover means covering the strips prior to their being separated, the strips being of an adhesive material and the cover means covering the adhesive material until removed by a user prior to use of the device thereby making the device easy to fit about a person's head, the cover means being in place when the device is so fitted, the cover means then being removed for the strips to be used in fitting the ventilator tube in place.

2. The device of claim 1 wherein the entire piece of material has an adhesive backing.

3. The device of claim 2 wherein a center portion of the material, which fits behind the person's head when the device is positioned for securing the ventilator tube in place, has a non-adhesive backing so the material does not stick to or irritate hair and skin on the back of the person's head.

4. The device of claim 1 further including package means in which the device is stored prior to use, the respective ends of the material being in one piece when the device is packaged and separated into strips after the device is removed from its package.

5. The device of claim 4 wherein the packaging means comprises a package for the device, said package including means for enclosing and sealing the device within the package.

6. The device of claim 1 wherein the material is a stretchable material that is deformable to fit around the person's head.

7. The device of claim 1 wherein the material is a cloth material.

* * * * *

UNITED STATES PATENT AND TRADEMARK OFFICE
CERTIFICATE OF CORRECTION

PATENT NO. : 5,546,938
DATED : August 20, 1996
INVENTOR(S) : Shirley T. McKenzie It is certified that error appears in the above-indentified patent and that said Letters Patent is hereby corrected as shown below:

```
                    Item [57]
                    In the Abstract
                    Line 1

After - "attaching and"
                    INSERT - "holding a ventilator" -
```

Signed and Sealed this

Seventh Day of October, 1997

Attest:

BRUCE LEHMAN

Attesting Officer   Commissioner of Patents and Trademarks